(12) United States Patent
Salimbeni et al.

(10) Patent No.: US 7,999,068 B2
(45) Date of Patent: Aug. 16, 2011

(54) PROCESS FOR THE PREPARATION OF BICYCLIC PEPTIDE COMPOUNDS

(75) Inventors: Aldo Salimbeni, Milan (IT); Davide Poma, Vimercate (IT); Damiano Turozzi, Turbigo (IT); Stefano Manzini, Florence (IT); Carlo Alberto Maggi, Florence (IT)

(73) Assignee: Menarini Ricerche S.p.A., Pomezia (IT)

( * ) Notice: Subject to any disclaimer, the term of this patent is extended or adjusted under 35 U.S.C. 154(b) by 1493 days.

(21) Appl. No.: 10/537,731

(22) PCT Filed: Dec. 4, 2003

(86) PCT No.: PCT/EP03/13696

§ 371 (c)(1),
(2), (4) Date: Apr. 17, 2006

(87) PCT Pub. No.: WO2004/052923

PCT Pub. Date: Jun. 24, 2004

(65) Prior Publication Data

US 2009/0163695 A1 Jun. 25, 2009

(30) Foreign Application Priority Data

Dec. 6, 2002 (IT) ................................ FI2002A0239

(51) Int. Cl.
*C07K 7/56* (2006.01)
(52) U.S. Cl. ...................................................... 530/317
(58) Field of Classification Search ........................ None
See application file for complete search history.

(56) References Cited

FOREIGN PATENT DOCUMENTS

WO   WO 96/28467 A   9/1996

OTHER PUBLICATIONS

Definition of derivative from http://cancerweb.ncl.ac.uk/cgi-bin/omd?query=derivtive, pp. 1-5. Accessed Jul. 7, 2005.*
Weisshoff H et al: "Structure determination and by-product profile of the NK2 receptor antagonist nepadutant, a bycyclic glycopeptid"; FEBS Letters, Elsevier Science Publishers, Amsterdam, NL, vol. 491, No. 3; Mar. 2, 2001, pp. 299-304.
Anisfeld S T et al: "A Convergent Approach to the Chemical Synthesis of Asparagine-Linked Glycopeptides" Journal of Organic Chemistry, vol. 55, No. 21, 1990, pp. 5560-5562, XP002288954, ISSN: 0022-3263.
Offer J et al: "On-Resin Solid-Phase Synthesis of Asparagine N-Linked Glycopeptides:Use of N-(2-Acetoxy-4-Methoxybenzyl)(AcHmb) Aspartyl Amide-Bond Protection to Prevent Unwanted Aspartimide Formation" Journal of the Chemical Society, Perkin Transactions 1, Chemical Society. Letchworth, GB, vol. 2, 1996, pp. 175-182, XP002055030; ISSN: 0300-922X.
Tuchalski, Gisbert et al: "Large scale synthesis of biologically active bicyclic hexapeptides";Peptides 1996, Proceedings of the European Peptide Symposium, 24th, Edinburgh, Sep. 8-13, 1996 (1998), Meeting date 1996, 845-846. Editor(s) Ramage, Robert; Epton, Roger. Publisher: Mayflower Scientific, Kingswinford, UK., 1998; XP009028177.
Akaji, K et al: "Synthesis of MEN 11420, a glycosylated bicyclic peptide using a chloroimidazlinium coupling reagent", Tetrahedron, Elsevier Science Publishers, Amsterdam, NL, vol. 57, No. 9, Feb. 25, 2001, pp. 1749-1755, XP004317634; ISSN: 0040-4020.
Caciagli V et al: "Large Scale Production of Peptides Using the Solid-Phase Continuous Flow Method. Preparative Synthesis of the Novel Tachykinin Antagonist MEN 10327" Journal of Peptide Science, John Wiley and Sons Ltd, GB, vol. 3, No. 3, May 1997, pp. 224-230, XP009028229; ISSN: 1075-2617.
International Search Report; Jul. 12, 2004; 7 pgs.; T.Vogt.
Davis Benjamin G: "Synthesis of glycoproteins." Chemical Reviews, Feb. 2002, vol. 102, No. 2, Feb. 2002, pp. 579-601, XP002288955, ISSN: 0009-2665.

* cited by examiner

*Primary Examiner* — Julie Ha
(74) *Attorney, Agent, or Firm* — Abelman, Frayne & Schwab

(57) ABSTRACT

A new process for the preparation of bicyclic peptide compounds Formula (I) in high yields of high purity, useful as intermediates for preparing compounds with pharmacological activity, is described.

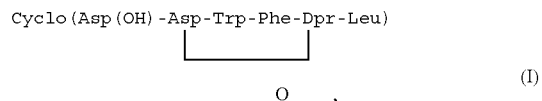

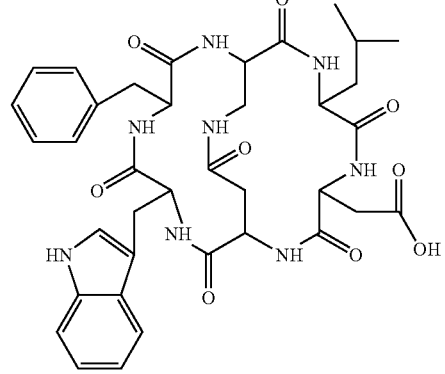

15 Claims, No Drawings

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: pentapeptide
<220> FEATURE:
<221> NAME/KEY: BINDING
<222> LOCATION: (1)..(1)
<223> OTHER INFORMATION: Asp is bound to a benzyloxycarbonyl group
<220> FEATURE:
<221> NAME/KEY: MISC_FEATURE
<222> LOCATION: (4)..(4)
<223> OTHER INFORMATION: X is Dpr (i.e. 2,3-diaminopropionic acid)
<220> FEATURE:
<221> NAME/KEY: MOD_RES
<222> LOCATION: (5)..(5)
<223> OTHER INFORMATION: METHYLATION

<400> SEQUENCE: 1

Asp Trp Phe Xaa Leu
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: cyclic pentapeptide
<220> FEATURE:
<221> NAME/KEY: BINDING
<222> LOCATION: (1)..(1)
<223> OTHER INFORMATION: Asp is bound to a benzyloxycarbonyl group
<220> FEATURE:
<221> NAME/KEY: SITE
<222> LOCATION: (1)..(4)
<223> OTHER INFORMATION: Asp and Dpr are bound together to form a cycle
<220> FEATURE:
<221> NAME/KEY: MISC_FEATURE
<222> LOCATION: (4)..(4)
<223> OTHER INFORMATION: X is Dpr (i.e. 2,3-diaminopropionic acid)
<220> FEATURE:
<221> NAME/KEY: MOD_RES
<222> LOCATION: (5)..(5)
<223> OTHER INFORMATION: METHYLATION

<400> SEQUENCE: 2

Asp Trp Phe Xaa Leu
1               5

<210> SEQ ID NO 3
<211> LENGTH: 5
<212> TYPE: PRT
<213> ORGANISM: Artificial Sequence
<220> FEATURE:
<223> OTHER INFORMATION: cyclic pentapeptide
<220> FEATURE:
<221> NAME/KEY: BINDING
<222> LOCATION: (1)..(1)
<223> OTHER INFORMATION: Asp is bound to a benzyloxycarbonyl group
<220> FEATURE:
<221> NAME/KEY: SITE
<222> LOCATION: (1)..(4)
<223> OTHER INFORMATION: Asp and Dpr are bound together to form a cycle
<220> FEATURE:
<221> NAME/KEY: MISC_FEATURE
<222> LOCATION: (4)..(4)
<223> OTHER INFORMATION: X is Dpr (i.e. 2,3-diaminopropionic acid)

<400> SEQUENCE: 3

Asp Trp Phe Xaa Leu
1               5

<210> SEQ ID NO 4
<211> LENGTH: 6
<212> TYPE: PRT
<213> ORGANISM: Artificial Sequence
<220> FEATURE:
<223> OTHER INFORMATION: cyclic hexapeptide
<220> FEATURE:
<221> NAME/KEY: BINDING
<222> LOCATION: (1)..(1)
<223> OTHER INFORMATION: Asp is bound to a benzyloxycarbonyl group and
      to a tert-butyl group
<220> FEATURE:
<221> NAME/KEY: SITE
<222> LOCATION: (2)..(5)
<223> OTHER INFORMATION: Asp and Dpr are bound together to form a cycle
<220> FEATURE:
<221> NAME/KEY: MISC_FEATURE
<222> LOCATION: (5)..(5)
<223> OTHER INFORMATION: X is Dpr (i.e. 2,3-aminopropionic acid)

<400> SEQUENCE: 4

Asp Asp Trp Phe Xaa Leu
1               5
```

-continued

```
<210> SEQ ID NO 5
<211> LENGTH: 6
<212> TYPE: PRT
<213> ORGANISM: Artificial Sequence
<220> FEATURE:
<223> OTHER INFORMATION: bicyclic hexapeptide
<220> FEATURE:
<221> NAME/KEY: SITE
<222> LOCATION: (1)..(6)
<223> OTHER INFORMATION: Asp and Leu are bound together to form a cycle
<220> FEATURE:
<221> NAME/KEY: BINDING
<222> LOCATION: (1)..(1)
<223> OTHER INFORMATION: Asp is bound to a tert-butyl group
<220> FEATURE:
<221> NAME/KEY: SITE
<222> LOCATION: (2)..(4)
<223> OTHER INFORMATION: Asp and Dpr are bound together to form a cycle
<220> FEATURE:
<221> NAME/KEY: MISC_FEATURE
<222> LOCATION: (5)..(5)
<223> OTHER INFORMATION: X is Dpr (i.e. 2,3-diaminopropionic acid)

<400> SEQUENCE: 5

Asp Asp Trp Phe Xaa Leu
1               5

<210> SEQ ID NO 6
<211> LENGTH: 6
<212> TYPE: PRT
<213> ORGANISM: Artificial Sequence
<220> FEATURE:
<223> OTHER INFORMATION: bicyclic hexapeptide
<220> FEATURE:
<221> NAME/KEY: SITE
<222> LOCATION: (1)..(6)
<223> OTHER INFORMATION: Asp and Leu are bound together to form a cycle
<220> FEATURE:
<221> NAME/KEY: SITE
<222> LOCATION: (2)..(5)
<223> OTHER INFORMATION: Asp and Dpr are bound together to form a cycle
<220> FEATURE:
<221> NAME/KEY: MISC_FEATURE
<222> LOCATION: (5)..(5)
<223> OTHER INFORMATION: X is Dpr (i.e. 2,3-diaminopropionic acid)

<400> SEQUENCE: 6

Asp Asp Trp Phe Xaa Leu
1               5

<210> SEQ ID NO 7
<211> LENGTH: 6
<212> TYPE: PRT
<213> ORGANISM: Artificial Sequence
<220> FEATURE:
<223> OTHER INFORMATION: bicyclic glycopeptide
<220> FEATURE:
<221> NAME/KEY: SITE
<222> LOCATION: (1)..(6)
<223> OTHER INFORMATION: Asp and Leu are bound together to form a cycle
<220> FEATURE:
<221> NAME/KEY: CARBOHYD
<222> LOCATION: (1)..(1)
<223> OTHER INFORMATION: Asp is bound to
      2-acetamide-3,4,6-tri-O-acetyl-2-deoxy-beta-D-glucopyranosylamine
<220> FEATURE:
<221> NAME/KEY: SITE
<222> LOCATION: (2)..(5)
<223> OTHER INFORMATION: Asp and Dpr are bound together to form a cycle
<220> FEATURE:
<221> NAME/KEY: MISC_FEATURE
<222> LOCATION: (5)..(5)
<223> OTHER INFORMATION: X is Dpr (i.e. 2,3-diaminopropionic acid)
```

-continued

```
<400> SEQUENCE: 7

Asp Asp Trp Phe Xaa Leu
1               5

<210> SEQ ID NO 8
<211> LENGTH: 6
<212> TYPE: PRT
<213> ORGANISM: Artificial Sequence
<220> FEATURE:
<223> OTHER INFORMATION: bicyclic glycopeptide
<220> FEATURE:
<221> NAME/KEY: SITE
<222> LOCATION: (1)..(6)
<223> OTHER INFORMATION: Asp and Leu are bound together to form a cycle
<220> FEATURE:
<221> NAME/KEY: CARBOHYD
<222> LOCATION: (1)..(1)
<223> OTHER INFORMATION: Asp is bound to 2-acetamide-2-deoxy-beta-D-
      glucopyranosylamine
<220> FEATURE:
<221> NAME/KEY: SITE
<222> LOCATION: (2)..(5)
<223> OTHER INFORMATION: Asp and Dpr are bound together to form a cycle
<220> FEATURE:
<221> NAME/KEY: MISC_FEATURE
<222> LOCATION: (5)..(5)
<223> OTHER INFORMATION: X is Dpr (i.e. 2,3-diaminopropionic acid)

<400> SEQUENCE: 8

Asp Asp Trp Phe Xaa Leu
1               5

<210> SEQ ID NO 9
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: BINDING
<222> LOCATION: (1)..(1)
<223> OTHER INFORMATION: Trp is bound to a benzyloxycarbonyl group
<220> FEATURE:
<221> NAME/KEY: MISC_FEATURE
<222> LOCATION: (3)..(3)
<223> OTHER INFORMATION: X is Dpr (i.e. 2,3-diaminopropionic acid)
<220> FEATURE:
<221> NAME/KEY: BINDING
<222> LOCATION: (3)..(3)
<223> OTHER INFORMATION: Dpr is bound to a tert-butoxycarbonyl group
<220> FEATURE:
<221> NAME/KEY: MOD_RES
<222> LOCATION: (4)..(4)
<223> OTHER INFORMATION: METHYLATION

<400> SEQUENCE: 9

Trp Phe Xaa Leu
1

<210> SEQ ID NO 10
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (3)..(3)
<223> OTHER INFORMATION: X is Dpr (i.e. 2,3-diaminopropionic acid)
<220> FEATURE:
<221> NAME/KEY: BINDING
<222> LOCATION: (3)..(3)
<223> OTHER INFORMATION: Dpr is bound to a tert-butoxycarbonyl group
<220> FEATURE:
```

```
<221> NAME/KEY: MOD_RES
<222> LOCATION: (3)..(3)
<223> OTHER INFORMATION: METHYLATION

<400> SEQUENCE: 10

Trp Phe Xaa Leu
1

<210> SEQ ID NO 11
<211> LENGTH: 5
<212> TYPE: PRT
<213> ORGANISM: Artificial Sequence
<220> FEATURE:
<223> OTHER INFORMATION: pentapeptide
<220> FEATURE:
<221> NAME/KEY: BINDING
<222> LOCATION: (1)..(1)
<223> OTHER INFORMATION: Asp is bound to a tert-butoxy group and to a
      benzyloxycarbonyl group
<220> FEATURE:
<221> NAME/KEY: MISC_FEATURE
<222> LOCATION: (4)..(4)
<223> OTHER INFORMATION: X is Dpr (i.e. 2,3-diaminopropionic acid)
<220> FEATURE:
<221> NAME/KEY: BINDING
<222> LOCATION: (4)..(4)
<223> OTHER INFORMATION: Dpr is bound to a tert-butoxycarbonyl group
<220> FEATURE:
<221> NAME/KEY: MOD_RES
<222> LOCATION: (4)..(4)
<223> OTHER INFORMATION: METHYLATION

<400> SEQUENCE: 11

Asp Trp Phe Xaa Leu
1               5
```

PROCESS FOR THE PREPARATION OF BICYCLIC PEPTIDE COMPOUNDS

FIELD OF THE INVENTION

The present invention relates to a new process for the preparation of bicyclic peptide compounds of formula (I) hereinafter reported, useful as intermediates in the preparation of pharmacologically active compounds, and in particular in the preparation of bicyclic glycopeptides of formula (I-A) hereinafter reported, which possess antagonist activity of the tachykinin NK2 receptor.

STATE OF THE ART

Compounds of formula (I-A) and in particular the compound [N-4-(2-acetylamino-2-deoxy-β-D-glucopyranosyl)-L-asparaginyl-L-α-aspartyl-L-triptophyl-L-phenylalanyl-L-2,3-diaminopropionyl-L-leucyl]-C-4,2-N-3,5-lactam-C-1,6-N-2,1-lactam (compound of formula (I-A) hereinafter reported, in which $R_1=R_2=R_3=H$, known with the trade name "Nepadutant") are compounds having a strong antagonist activity of the tachykinin NK2 receptor, and can therefore be used for preparing pharmaceutical compounds for treating diseases, useful in the treatment and prevention of diseases where tachykinins are implicated as neuromodulators.

This compound and some of its intermediates are described in the European Patent No. 815 126 B1, particularly in Example 4. This document describes, on pages 4 and 5, the methods, already known in the literature, of synthesis in solution or in solid phase of linear peptides by sequential coupling of suitably protected amino acids and their subsequent final cyclization, in order to obtain compounds of general formula (I).

These methods have been described in a very general way, while more details have been provided for preparing the compounds in Examples 1 and 2. In these examples, the synthesis used was the coupling of Fmoc amino acids in solid phase until a linear peptide was obtained which, after detachment from the resin, is cyclized, purified by HPLC and cyclized again. It is important to note that, following to this path of synthesis, the glycosidic pendant is introduced at the stage of synthesis in solid phase of the linear peptide on the resin, as a side chain suitably protected of Asparagine.

SUMMARY OF THE INVENTION

The Applicant has now surprisingly found a new and more efficient process for the preparation of bicyclic peptide compounds of formula (I) hereinafter reported, useful as intermediates for preparing compounds with pharmacological activity.

The new process is carried out entirely in solution rather than in solid phase and allows products with high purity and high yields to be obtained.

It is therefore subject of the present invention a process for the preparation of bicyclic peptide compounds of formula (I) (SEQ. ID. 1)

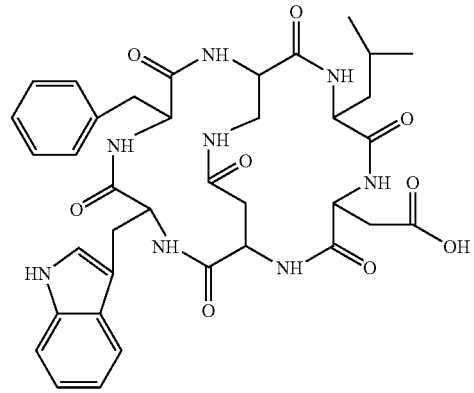

Cyclo(Asp(OH)-Asp-Trp-Phe-Dpr-Leu)  (I)

comprising the following steps:
1) deprotection of the linear pentapeptide of formula (II) (SEQ. ID. 2) in the presence of a solvent to give the compound of formula (III):

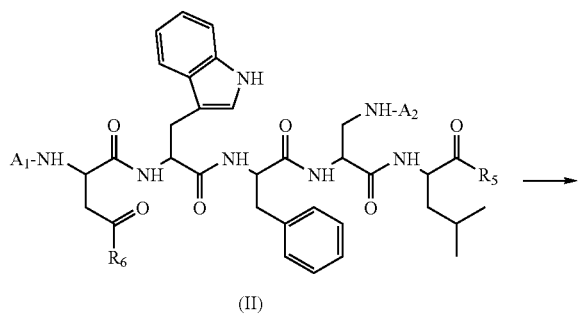

$A_1$-Asp($R_6$)-Trp-Phe-Dpr($A_2$)-Leu-$R_5$ (II)

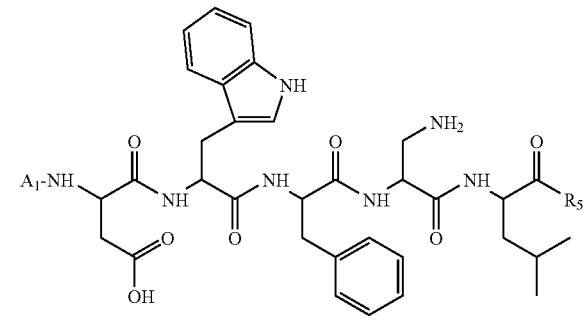

$A_1$-Asp(OH)-Trp-Phe-Dpr(H)-Leu-$R_5$ (III)

wherein $A_1$ and $A_2$ are two nitrogen protecting groups different from each other, and $R_5$ and $R_6$, different from each other, are chosen from benzyloxy and lower alkyloxy groups in which the alkyl part comprises a linear or branched C1-C4 group;

2) intramolecular cyclisation of the compound of formula (III) coming from step 1) in the presence of a solvent and of a suitable coupling agent to give the compound of formula (IV) (SEQ. ID. 3):

A₁-Asp(OH)-Trp-Phe-Dpr(H)-Leu-R₅

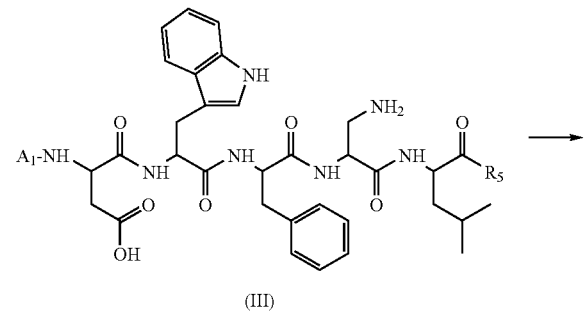

(III)

A₁-Asp-Trp-Phe-Dpr-Leu-R₅
       └─────────────┘

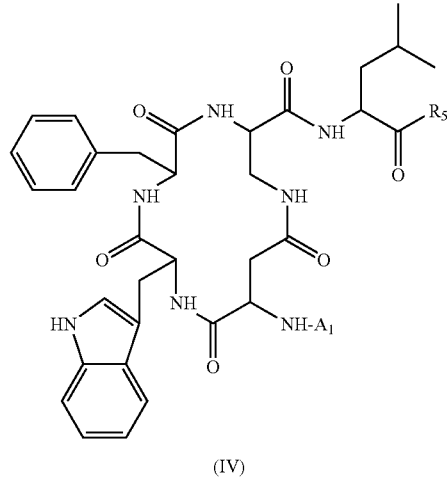

(IV)

wherein R₅ is as defined above;

3) deprotection of the compound of formula (IV) coming from step 2) in the presence of a solvent to give the compound of formula (V)

A₁-Asp-Trp-Phe-Dpr-Leu-R₅
       └─────────────┘

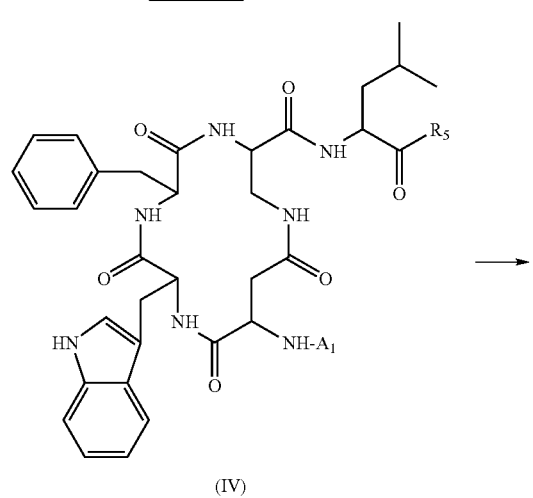

(IV)

-continued

H-Asp-Trp-Phe-Dpr-Leu-OH
       └─────────────┘

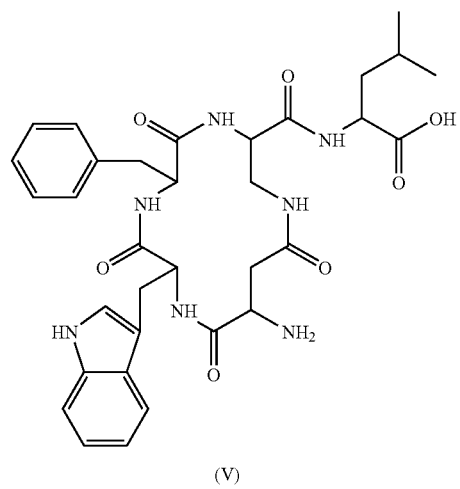

(V)

wherein R₅ is as defined above;

4) coupling between the compound of formula (V) coming from step 3) and a protected amino-acid of formula (VIa) in the presence of a solvent, to give compounds of formula (VII) (SEQ. ID. 4):

H-Asp-Trp-Phe-Dpr-Leu-OH
       └─────────────┘

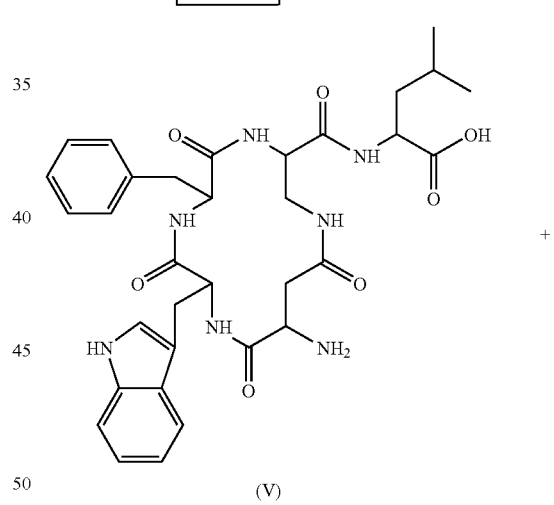

(V)

+

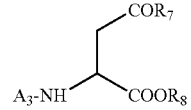

(VIa)

-continued

A$_3$-Asp(R$_7$)-Asp-Trp-Phe-Dpr-Leu-OH

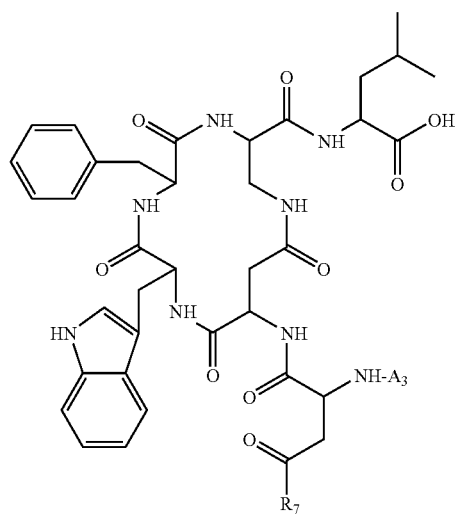

(VII)

wherein A$_3$ is a nitrogen protecting group; R$_7$ is chosen from benzyloxy and lower alkyloxy groups, in which the alkyl part comprises a linear or branched C1-C4 group; R$_8$ is a residual group deriving from an activation procedure on the carboxyl group;

5) deprotection of the compound of formula (VII) coming from step 4) in the presence of a solvent to give a compound of formula (VIII)

A$_3$-Asp(R$_7$)-Asp-Trp-Phe-Dpr-Leu-OH

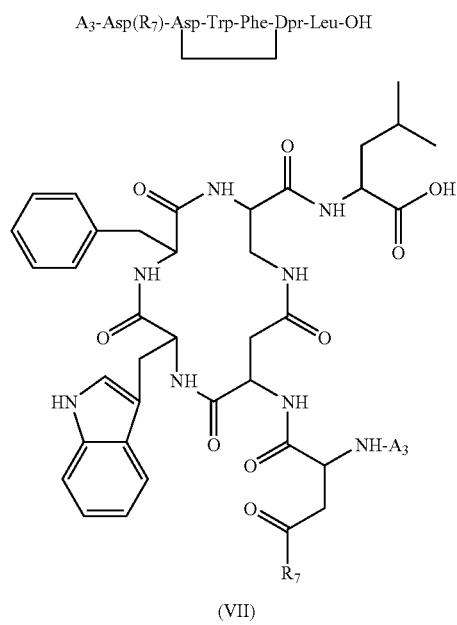

(VII)

-continued

H-Asp(R$_7$)-Asp-Trp-Phe-Dpr-Leu-OH

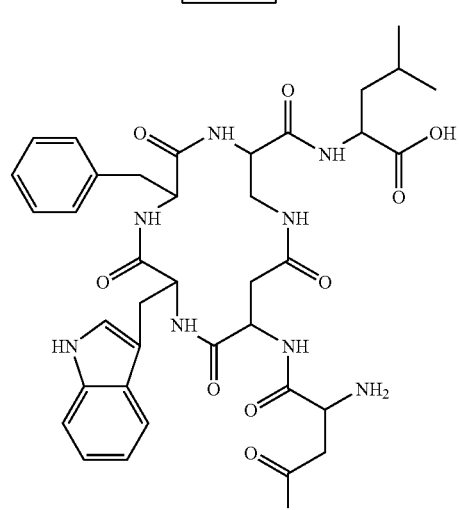

(VIII)

wherein R$_7$ is as defined above;

6) intramolecular cyclisation, in the presence of a solvent and of a suitable coupling agent, of the compound of formula (VIII) coming from step 5) to give a bicyclic compound of formula (IX)

H-Asp(R$_7$)-Asp-Trp-Phe-Dpr-Leu-OH

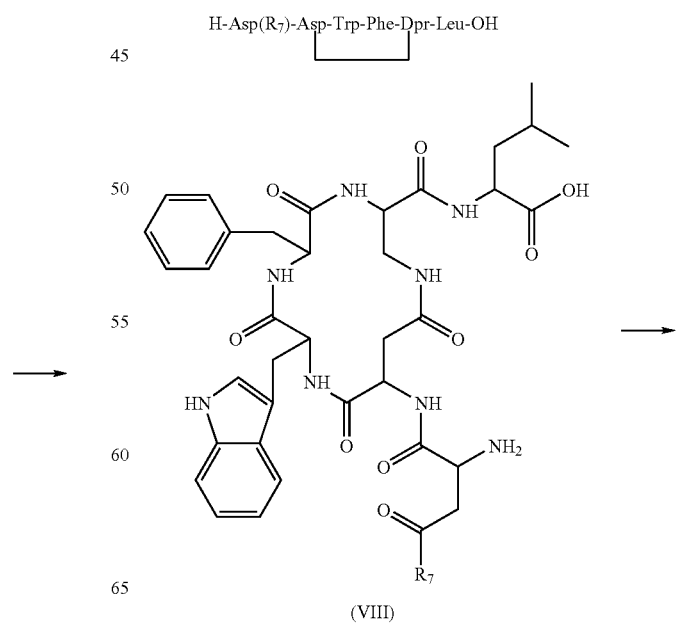

(VIII)

-continued

Ciclo(Ciclo(Asp(R7)-Asp-Trp-Phe-Dpr-Leu)

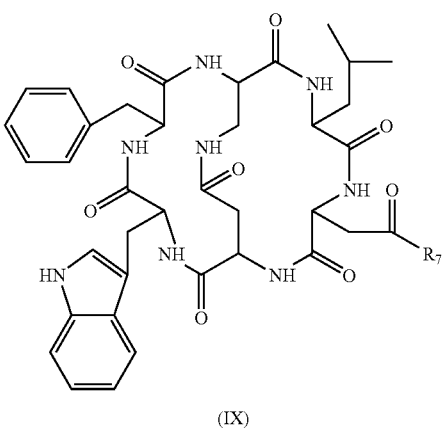

(IX)

wherein R₇ is as defined above;

7) deprotection of the bicyclic compound of formula (IX) coming from step 6) in the presence of a solvent, to obtain the compound of formula (I)

Ciclo(Asp(R7)-Asp-Trp-Phe-Dpr-Leu)

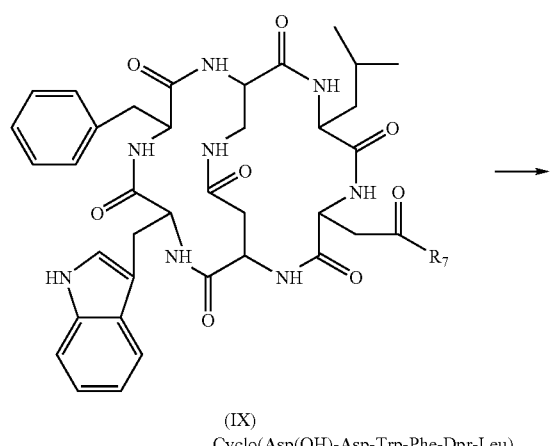

(IX)

Cyclo(Asp(OH)-Asp-Trp-Phe-Dpr-Leu)

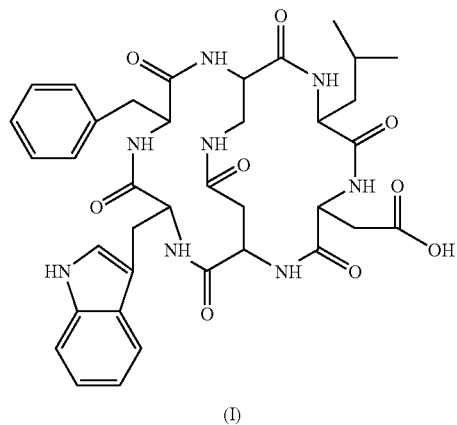

(I)

wherein R₇ is as defined above.

Compound of formula (III) is represented by SEQ. ID. 2 wherein

The compounds of formula (I) can be used for example for the preparation of bicyclic glycopeptide compounds of formula (I-A) hereinafter reported, which possess a powerful antagonist activity towards the tachykinin $NK_2$ receptor; the Applicant has found a new preparation process, whereby a glycosidic pendant is introduced into compounds of formula (I) by a reaction carried out in solution, and the purification of the final product by HPLC is not necessary, so that large scale production of these compounds can be achieved at decidedly lower costs than those of the current production process.

A further subject of the present invention is a process for the preparation of bicyclic glycopeptide compounds of formula (I-A) (SEQ. ID. 5)

(I-A)

wherein $R_1$, $R_2$ and $R_3$, equal or different from each other, can be hydrogen or an oxygen protecting group, comprising the following steps:

1A) activation of bicyclic peptide compounds of formula (I) with a suitable coupling agent to obtain a derivative of formula (II-A)

Ciclo(Asp(OH)-Asp-Trp-Phe-Dpr-Leu)

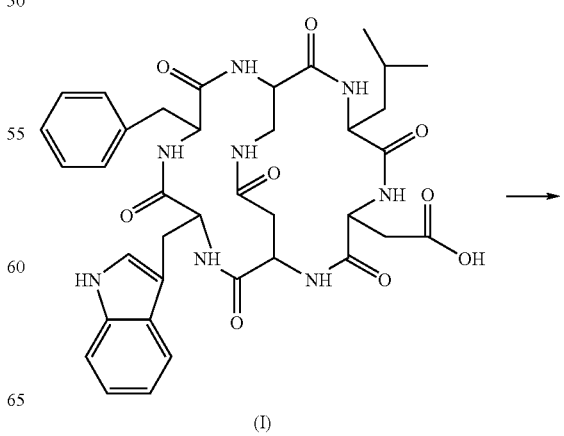

(I)

-continued

Ciclo(Asp(OR)-Asp-Trp-Phe-Dpr-Leu)

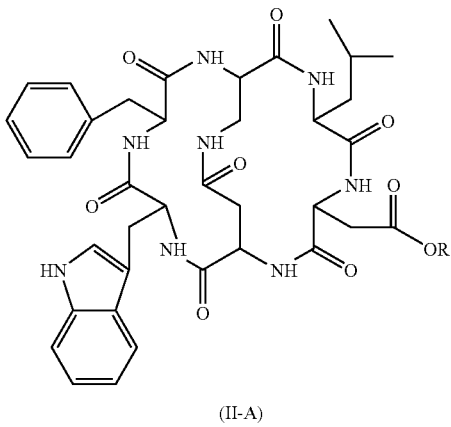

(II-A)

wherein R is selected from the group consisting of benzotriazole, possibly substituted with a halogen, azabenzotriazole and succinimidyl;

2A) reaction of the compound of formula (II-A) coming from step 1A) in the presence of a solvent with a glycosidic derivative of formula (III-A)

Ciclo(Asp(OR)-Asp-Trp-Phe-Dpr-Leu)

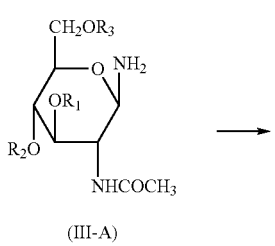

(II-A)

+

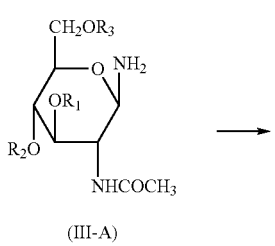

(III-A)

-continued

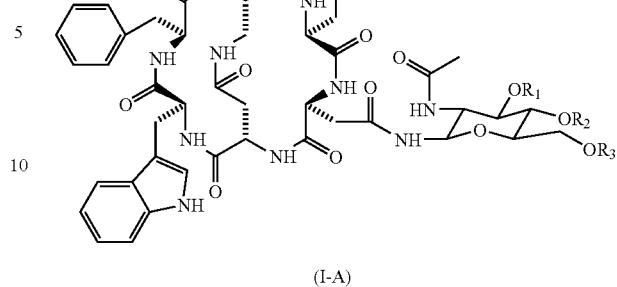

(I-A)

wherein R, $R_1$, $R_2$ and $R_3$ are as defined above.

A further subject of the invention is a process for preparing the compound of formula (1-A) starting from the compounds of formula (II) and formula (III), passing via the formation of the compound of formula (I) as described in the two aforementioned processes.

The processes of the invention, carried out entirely by means of reactions in solution rather than in solid phase, show unexpectedly high yields and do not require the use of HPLC purification processes, thus allowing a significant reduction of the production costs and enabling large scale preparation to be achieved.

DETAILED DESCRIPTION OF THE INVENTION

The nitrogen protecting groups used in the present processes can be chosen from any of the protecting groups that can be used for peptide synthesis such as those reported in M. Bodansky, "*Peptide Chemistry*", Springer Verlag 1988 or in J. Jones, "*The Chemical Synthesis of Peptides*", Clarendon Press. Oxford 1994. According to the invention, the nitrogen protecting groups are preferably selected from the group consisting of benzyloxycarbonyl and alkoxy carbonyl in which the alkyl part comprises a linear or branched C1-C4 group; more preferably they are chosen from t-butoxycarbonyl (Boc) and benzyloxycarbonyl (Z).

$R_8$ is a residual group deriving from an activation procedure, preferably chosen from the group consisting of benzyloxycarbonyl, alkoxycarbonyl comprising in the alkyl part a linear or branched C1-C4 group, succinimidyl, benzotriazole possibly substituted by a halogen, and azabenzotriazole.

The linear peptides of formula (II) can be prepared by one of the following strategies:

a) Stepwise strategy: with this strategy the amino acids necessary for obtaining the peptide of formula (II) are sequentially coupled starting from a derivative of the amino acid Dpr of formula (X), protected on nitrogen and prepared separately or generated in situ

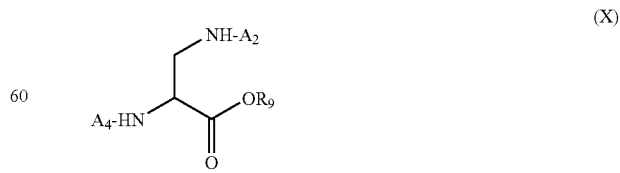

(X)

wherein:

$A_2$ and $A_4$, different from each other, are nitrogen protecting groups, as defined above;

R$_9$ is a residual group deriving from an activation procedure, preferably chosen from the group consisting of benzyloxycarbonyl, alkoxycarbonyl comprising in the alkyl part a linear or branched C1-C4 group, and succinimidyl;

the derivative of formula (X) above reported is reacted with a Leu ester (XI) in the presence of a solvent

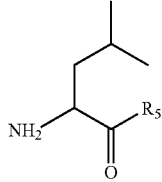

(XI)

wherein R$_5$ is defined as above, thus obtaining the dipeptide A$_4$-Dpr(A$_2$)-Leu-R$_5$, which is then deprotected by a suitable method depending on the protecting group on nitrogen to be removed, and compatible with the protecting group to be maintained.

The dipeptide thus deprotected is subsequently coupled with the activated ester of the amino acid Phe, and so on in sequence with Trp and Asp until the compounds of formula (II) are obtained.

b) Strategy 2+2+1: this strategy consists of coupling the monodeprotected dipeptide H-Dpr(A$_2$)-Leu-R$_5$ obtained as described above according to strategy a), with an activated derivative of the dipeptide having the following formula (XII)

A$_5$-Trp-Phe-OH   (XII)

wherein A$_2$ and A$_5$, different from each other, are nitrogen protecting groups, as defined above;

prepared separately or generated in situ by coupling an activated ester of a Trp protected on nitrogen prepared separately or generated in situ, with a Phe ester and subsequent hydrolysis of the ester group.

The resulting tetrapeptide A$_5$-Trp-Phe-Dpr(A$_2$)Leu-R$_5$ is suitably deprotected from the group attached to the nitrogen of Trp and coupled with a compound of formula (VIb)

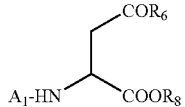

(VIb)

wherein

A$_1$, R$_6$ and R$_8$ are defined as above.

c) Strategy 3+2: according to this strategy the tripeptide A$_1$-Asp(R$_6$)-Trp-Phe-OH, obtained by removing the nitrogen protecting group from the compounds of formula (XII) above reported, and subsequent coupling with a compound of formula (VIb) above reported, is then coupled with the monodeprotected dipeptide H-Dpr-(A$_2$)-Leu-R$_5$ prepared as described according to the procedure of strategy a).

As used in the present invention, the term "lower alkoxyl groups" refers to those alkoxyl groups in which the alkyl part comprises a linear or branched C1-C4 group, preferably selected from the group consisting of methyl, ethyl, propyl, butyl, isopropyl and t-butyl. This should be meant also for the alkyloxycarbonyl groups of the invention, in which the alkyl part comprises a linear or branched C1-C4 group, preferably selected from the group consisting of methyl, ethyl, propyl, butyl, isopropyl and t-butyl.

The coupling agent can be chosen from any one of those more commonly used in peptide synthesis, so as to generate an activated amino acid derivative such as those reported for example in M. Bodansky, "*Peptide Chemistry*," Springer Verlag 1988 or in J. Jones, "*The Chemical Synthesis of Peptides*", Clarendon Press. Oxford 1994.

The activated derivatives, if not commercially available, can be prepared separately or in situ by reaction between an amino acid or a peptide and one or more of the numerous known coupling agents, such as isobutyl chloroformate (IBCF), a carbodiimide selected from dicyclohexylcarbodiimide (DCC) and 1-ethyl-3-(3-dimethylaminopropyl)carbodiimide hydrochloride (EDAC.HCl) possibly in combination with a hydroxyderivative selected from 1-hydroxybenzotriazole (HOBt), 1-hydroxy-7-azabenzotriazole (HOAt), 6-chloro-1-hydroxybenzotriazole (Cl—HOBt) and hydroxysuccinimide (HOSu); a phosphonium salt, N-oxide guanidine salt or uronium salt, such as (Benzotriazol-1-yloxy)tri(dimethylamino)phosphonium hexafluorophosphate (BOP), (Benzotriazol-1-yloxy)tripyrrolidine phosphonium hexafluorophosphate (PyBOP), 1-[bis(dimethylamino)methylene]-1H-benzothiazolium-3-oxide hexafluorophosphate (HBTU), 1-[bis(dimethylamino)methylene]-5-chloro-1H-benzothiazolium-3-oxide hexafluorophosphate (HCTU), 1-[bis(dimethylamino)methylene]-1H-benzothiazolium-3-oxide tetrafluoroborate (TBTU), 1-[bis(dimethylamino)methylene]-1H-1,2,3-triazole[4,5-b]pyridinium-3-oxide hexafluorophosphate (HATU), 1-[bis(dimethylamino)methylene]-5-chloro-1H-benzothiazolium-3-oxide tetrafluoroborate (TCTU), O-[(ethoxycarbonyl)cyanomethylenamino]-N,N,N',N'-tetramethyluronium tetrafluoroborate (TOTU), O-(bicyclo[2.2.1]hept-5-ene-2,3-dicarboximido)-N,N,N',N'-tetramethyluronium tetrafluoroborate (TNTU), or O—(N-succinimidyl)-N,N,N',N'-tetramethyluronium tetrafluoroborate (TSTU).

Where the derivative is generated in situ the coupling reaction is carried out immediately afterwards by adding the other reagent, which obviously, in the case of intramolecular cyclizations, corresponds to the free amine end present in the molecule itself.

The coupling reaction is usually carried out in the presence of a tertiary amine such as N-methylmorpholine (NMM), triethylamine (TEA) or diisopropylethylamine (DIPEA) in an organic solvent chosen from those generally used for peptide synthesis. Preferred solvents for the coupling reaction are ethyl acetate (AcOEt), dimethylformamide (DMF) and N-methylpyrrolidone (NMP).

The coupling reactions can be carried out at a temperature that would not cause degradations or render the reaction too slow, the temperature being preferably comprised between −20 and +50° C.

The deprotections in the processes of the invention are achieved by the appropriate methods for groups to be removed and compatible with the groups to be retained; generally the present deprotection reactions are carried out by means of catalytic hydrogenation or by acid or base treatments.

For hydrogenations, the catalyst can be chosen from those varieties of catalysts which are available and suitable for this purpose; 5% or 10% Palladium are preferred. The solvent for the deprotection reactions by catalytic hydrogenation can be chosen from those that dissolve the compounds in reaction, excluding ketones such as acetone, the solvents which poison the catalyst and those that react with the components of the reaction themselves. DMF, NMP, organic acids such as acetic acid and p-toluene sulfonic acid (PTSA), and alcohols such as methanol, ethanol, and isopropanol, or mixtures thereof, are the preferred reaction solvents. The hydrogenation reaction temperature is comprised between −20 and +50° C.

For deprotections by acid treatment, mineral acids are preferably used, such as hydrochloric acid, or organic acids, such as trifluoroacetic acid or formic acid, which can be used alone or mixed with other solvents. The temperature is between −20 and +50° C.

For deprotections by basic treatment, hydroxides of alkali metals and alkaline earth metals are preferably used in the presence of a solvent such as water, dioxane, acetonitrile, methanol, ethanol, isopropanol, or mixtures thereof; the temperature is comprised between −20 and +50° C.

The term "oxygen protecting group" as used in the present invention refers to a protecting group selected from those commonly used for the protection of —OH groups and well known to any person skilled in the art, selected for example from the group consisting of —$COR_4$ wherein $R_4$ is a linear or branched alkyl group, with from 1 to 4 carbon atoms, the phenyl being possibly substituted by a halogen atom, benzyl or benzoyl; the oxygen protecting group is preferably acetyl.

According to the invention the glycopeptide compounds of formula (I-A) can be obtained by reacting a glycosidic derivative of formula (III-A) with an activated peptide derivative of formula (II-A), obtained by an activation reaction or generated in situ by a compound of formula (I). Therefore, in the preparation process of bicyclic glycopeptide compounds of formula (1-A), the glycosidic group is introduced not in the linear peptide, but in the bicyclic peptide compound.

If compounds of formula (III-A) are reacted in which $R_1$, $R_2$ and $R_3$ are not hydrogen, the compounds of formula (I-A) obtained can be transformed into the corresponding compounds in which $R_1=R_2=R_3=H$, by means of catalytic hydrogenation or by an acid or base treatment according to the nature of the protecting groups $R_1$, $R_2$ and $R_3$.

The glycosidic compounds of formula (III-A) preferably used in the process of the invention are selected from the group consisting of 2-acetamide-2-deoxy-β-D-glucopyranosylamine and 2-acetamide-3,4,6-tri-O-acetyl-2-deoxy-β-D-glucopyranosylamine, which are known in the literature and can be prepared for example as described respectively in I. Shin et al., *Tetrahedron Letters*, 42 (2001) 1325-1328 and D. Macmillan et al., *Organic Letters*, Vol. 4, N° 9, 2002.

The following examples and schemes of synthesis are given to provide a non-limiting illustration of the invention.

Scheme 1 indicates the synthesis path which, starting from the compounds of formula (II) leads to those of formula (I-A), whereas schemes 2-4 show the three different strategies for preparing the compounds of formula (II).

The protecting groups shown as examples are t-butoxycarbonyl (BOC) and benzyloxycarbonyl (Z) for the amino extremities and methylester and t-butylester for the carboxyl extremities.

The numbers given beside each compound in the following schemes corresponds to the numbers attributed to the compounds in the examples.

The identification and evaluation of purity for the compounds prepared has been established by elemental analysis, HPLC, $^1$H-NMR, IR and mass analysis.

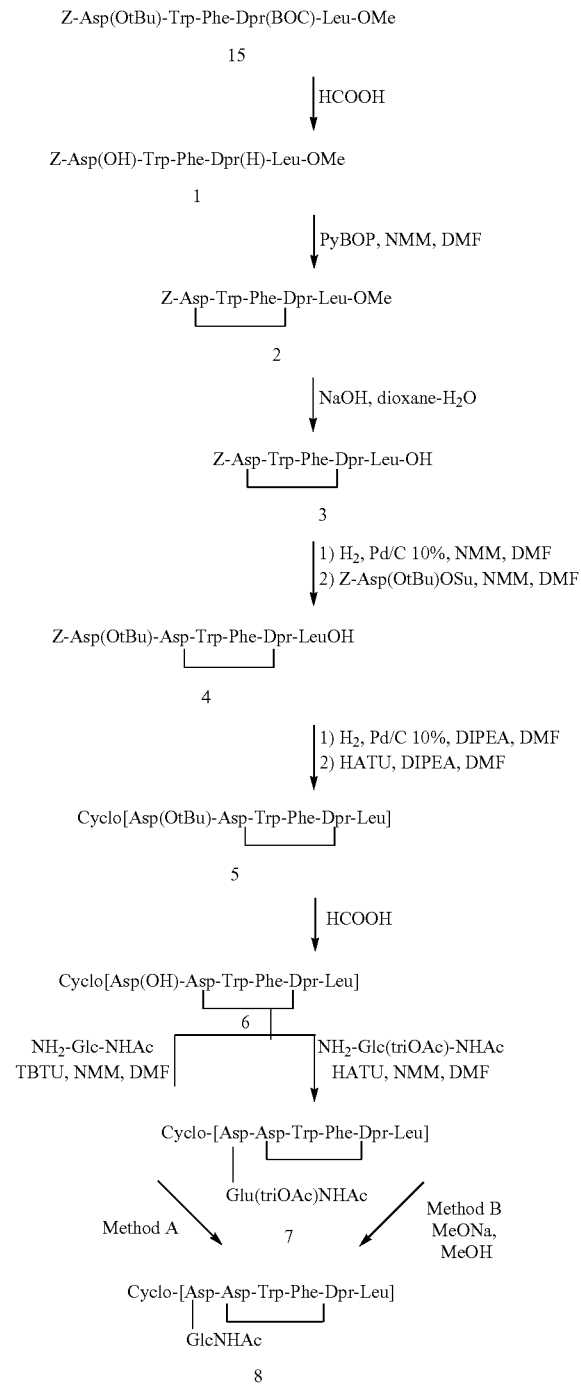

Scheme 1: synthesis of compounds of formula (I-A)

Scheme 2: synthesis of compounds of formula (II) as in strategy a) (stepwise strategy)

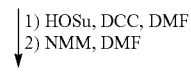

-continued

Z-Dpr(BOC)-Leu-OMe
9
↓ H₂, Pd/C 10%, MeOH, PTSA

[H-Dpr(BOC)-Leu-OMe]
10
↓ Z-Phe-OSu, NMM, DMF

Z-Phe-Dpr(BOC)-Leu-OMe
11
↓ H₂, Pd/C 10%, DMF

[H-Phe-Dpr(BOC)-Leu-OMe]
12
↓ Z-Trp-OSu, NMM, DMF

Z-Trp-Phe-Dpr(BOC)-Leu-OMe
13
↓ H₂, Pd/C 10%, NMP

[H-Trp-Phe-Dpr(BOC)-Leu-OMe]
14
↓ Z-Asp(OtBu)-Osu
DIPEA, NMP-CH₃CN

Z-Asp(OtBu)-Trp-Phe-Dpr(BOC)-Leu-OMe
15

Scheme 3: synthesis of compounds of formula (II) as in strategy b)
(strategy 2 + 2 + 1)

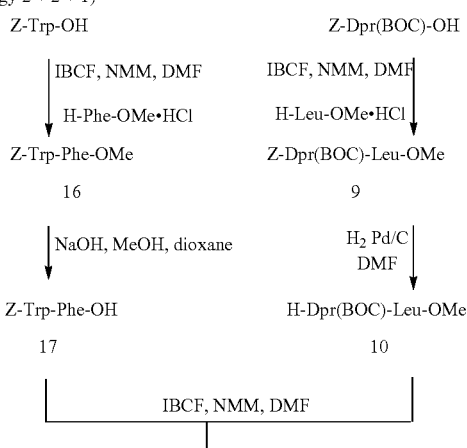

-continued

Z-Trp-Phe-Dpr(BOC)-Leu-OMe
13
↓ Pd/C, H₂, NMP
  Z-Asp(OtBu)-OSu, CH₃CN, DIPEA

Z-Asp(OtBu)-Trp-Phe-Dpr(BOC)-Leu-OMe
15

Scheme 4: synthesis of compounds of formula (II) as in stratagy c)
(strategy 3 + 2)

Z-Trp-OH                    Z-Dpr(BOC)-OH
↓ IBCF, NMM, DMF            IBCF, NMM, DMF ↓
  H-Phe-OMe·HCl             H-Leu-OMe·HCl
Z-Trp-Phe-OMe               Z-Dpr(BOC)-Leu-OMe
16                          9
↓ NaOH, CH₃OH               H₂ Pd/C ↓
                            DMF
Z-Trp-Phe-OH                [H-Dpr(BOC)-Leu-OMe]
17                          10
↓ H₂ Pd/C, CH₃COOH

H-Trp-Phe-OH
18
↓ Z-Asp(OtBu)-OSu,
  NMM, DMF

Z-Asp(OtBu)-Trp-Phe-OH
19
└──────── TBTU, DIPEA, DMF ────────┐
                                   ↓
Z-Asp(OtBu)-Trp-Phe-Dpr(BOC)-Leu-OMe
15

EXAMPLE 1

Preparation of Z-Asp(OH)-Trp-Phe-Dpr(H)-Leu-Ome (SEQ. ID. 1)

A 72 mmol/l solution of Z-Asp(OtBu)-Trp-Phe-Dpr(BOC)-Leu-OMe, prepared as described in Example 15, in 95% formic acid is heated to 40° C. under vacuum for 4 hours.

The reaction mixture is evaporated under reduced pressure and the residue is redissolved with a 8:2 CH₃CN—H₂O mixture.

The suspension is cooled to 15-20° C. and the pH is corrected to 6 by adding a 20% aqueous NMM solution.

The acetonitrile is evaporated under reduced pressure and the resulting suspension is filtered.

The whitish solid obtained is washed with H₂0 and dried under vacuum at 30-40° C. to provide a yield equal to 96.4%.

¹H-NMR dimethylsulfoxide-d₆ (DMSO-d₆) δ:
0.86 (2d; 6H); 1.47-1.75 (m; 3H); 2.32-2.68 (m; 2H); 2.79-3.55 (m; 6H); 3.63 (s; 3H); 4.25-4.65 (m; 5H); 4.99 (AB- Syst.; 2H); 6.91-7.43 (m; 14H); 7.48-7.60 (2d; 2H); 7.82 (b; 2H); 8.03-8.43 (4d; 4H); 10.83 (s; 1H); 12.35 (b; 1H).

EXAMPLE 2

Preparation of

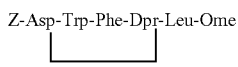 (SEQ. ID. 2)

2.2 equivalents of NMM are added to a 24 mmol/l solution of Z-Asp(OH)-Trp-Phe-Dpr($NH_2$)-Leu-Ome in DMF and after 5-10 minutes 1.2 equivalents of PyBOP are added.

After 2-3 hours of stirring at room temperature the solution is evaporated under reduced pressure until a fluid residue is obtained which is dropped into a 0.5 M aqueous solution of $NaHCO_3$.

The resulting suspension is filtered and the solid obtained is washed with a 4:6 DMF—$H_2O$ mixture and then with $H_2O$ until neutral pH is achieved and dried under vacuum at 30-50° C., providing a yield equal to 84.2%.

$^1$H-NMR (DMSO $d_6$) δ:

0.83 (2d; 6H); 1.34-1.69 (m; 3H); 2.31-2.92 (m; 4H); 3.03-3.91 (m; 4H); 3.61 (s; 3H); 4.17-4.63 (m; 5H); 5.01 (AB-Syst.; 2H); 6.84-7.48 (m; 16H); 7.60 (d; 1H); 7.87 (d; 2H); 8.01 (t; 1H); 8.27 (d; 1H); 10.81 (s; 1H).

EXAMPLE 3

Preparation of

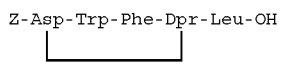 (SEQ. ID. 3)

A cloudy solution containing 77 mmol/l of

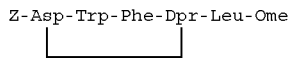

in a 8:2 dioxane —$H_2O$ mixture is heated to 35° C. and maintained at pH 12.0-12.5 by slowly and continuously adding 1.5 N NaOH.

At the end of the reaction the cloudy solution is brought to pH 9 by adding 6N HCl, clarified by filtration on a co-adjuvant filtration bed and acidified to pH 3 by again adding 6N HCl.

The solution is concentrated under reduced pressure until a filterable solution is obtained.

The whitish filtered solid is washed with a 1:1 dioxane —$H_2O$ mixture and then with $H_2O$ and dried under vacuum at 30-40° C., providing a yield equal to 97.7%.

$^1$H-NMR (DMSO-$d_6$) δ:

0.84 (2d; 6H); 1.42-1.76 (m; 3H); 2.29-3.48 (m; 7H); 3.85 (m; 1H); 4.10-4.65 (m; 5H); 5.00 (AB-Syst.; 2H); 6.86-7.47 (m; 16H); 7.55-8.36 (4d+m; 5H); 10.80 (d; 1H); 12.65 (b; 1H).

EXAMPLE 4

Preparation of

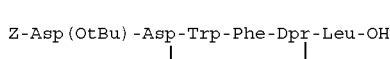 (SEQ. ID. 4)

A 66 mmol/l solution of

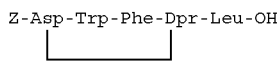

in DMF is hydrogenated at room temperature in the presence of 1 equivalent of NMM and catalytic quantities of 10% Pd/C, at 50% wetness.

After reacting for 6 hours the suspension is filtered to remove catalyst and filtrate is diluted with DMF to obtain a 53 mmol/l solution of

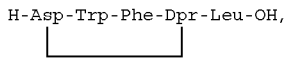

to which 4 equivalents of NMM and 1.05 equivalents of Z-Asp(OtBu)Osu are added.

After stirring for 5 hours at room temperature the mixture is evaporated under reduced pressure until a residue is obtained which is dropped into 0.05 $NH_2SO4$. The resulting suspension is filtered and the solid obtained is washed with a 1:1 DMF —$H_2O$ mixture and then with $H_2O$ and dried under vacuum at 30-40° C., to provide a yield equal to 93.7%.

$^1$H-NMR (DMSO-$d_6$) δ:

0.84 (2d; 6H), 1.35 (s; 9H); 1.40-1.70 (m; 3H); 2.20-3.94 (m; 10H); 4.10-4.81 (m; 6H); 4.92-5.12 (AB-Syst.; 2H); 6.74-7.57 (m; 17H); 7.71-8.35 (4d+1t; 5H); 10.70 (s; 1H); 12.70 (b; 1H).

EXAMPLE 5

Preparation of

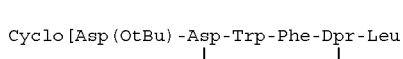 (SEQ. ID. 5)

A 47 mmol/l solution of

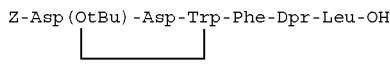

in DMF is hydrogenated at room temperature, in the presence of 1 equivalent of DIPEA and catalytic quantities of 10% Pd/C at 50% wetness.

After reacting for about 2 hours the suspension is filtered to remove the catalyst and diluted with DMF until a 19 mmol/l solution

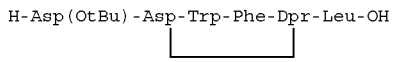

is obtained to which 1.4 equivalents of DIPEA and 1.2 equivalents of HATU are added.

After stirring for 30-60 minutes at room temperature the solution is evaporated under reduced pressure until a residue is obtained which is dropped into a 0.5 M aqueous solution of NaHCO$_3$.

The resulting suspension is filtered and the solid obtained is washed with abundant H$_2$O until the pH is neutral, and dried under vacuum at 30-50° C., obtaining a yield equal to 94.1%.

$^1$H-NMR (DMSO-d$_6$) δ:
0.88 (2d; 6H); 1.38 (s; 9H); 1.31-1.72 (m; 3H); 2.33-2.99 (m; 6H); 3.20-3.63 (m; 3H); 3.87-4.62 (m; 7H); 6.75-7.50 (m; 13H); 8.04 (b; 1H); 8.56 (d; 1H); 8.76 (d; 1H); 9.18 (b; 1H); 10.84 (s; 1H).

EXAMPLE 6

Preparation of

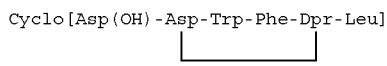
(SEQ. ID. 6)

A 83 mmol/l solution of

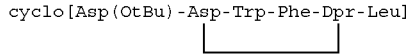

in 90% formic acid is heated at 40° C. under vacuum for 2 hours.

The reaction mixture is evaporated under reduced pressure until a dense residue is obtained which is redissolved in H$_2$O.

The resulting suspension is filtered and the solid obtained is washed with H$_2$O, dried under vacuum at 30-40° C. and finally purified by means of a Sephadex® LH-20 column, eluting with methanol.

314 g of a white solid are obtained (titre 95.2%, yield 82.0%).

$^1$H-NMR (DMSO-d$_6$) δ:
0.88 (2d; 6H); 1.31-1.77 (m; 3H); 2.32-3.73 (m; 9H); 3.80-4.65 (m; 7H); 6.82-7.51 (m; 13H); 7.94-9.19 (2d; 2b; 4H); 10.85 (s; 1H); 12.20 (s; 1H).

EXAMPLE 7

Preparation of

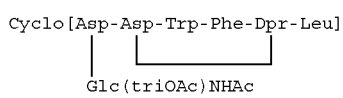
(SEQ. ID. 7)

3 equivalents of NMM, 1.2 equivalents of HATU and 2-acetamide-3,4,6-tri-O-acetyl-2-deoxy-β-D-glucopyranosylamine are added to a 0.24 mol/l solution of

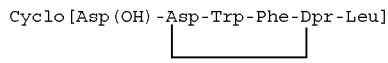

in DMF at 10 minute intervals.

After stirring for 1 hour at 0-4° C. the reaction mixture is evaporated under reduced pressure until a fluid residue is obtained which is dropped into a 1% aqueous solution of NaHCO$_3$.

The resulting suspension is filtered and the solid obtained is washed with H$_2$O, dried under vacuum at 30-40° C. and purified by crystallization from a EtOH—H$_2$O mixture.

117 g of a white solid are obtained (titre 96.0%, yield 87.0%).

$^1$H-NMR (DMSO-d$_6$) δ:
10.80 (d; 1H); 8.90 (b; 1H); 8.72 (d; 1H); 8.47 (d; 1H); 8.46 (d; 1H); 8.08 (b; 1H); 7.84 (d; 1H); 7.43 (dd; 1H); 7.33 (dd; 1H); 7.24 (b; 1H); 7.23 (m; 2H); 7.16 (m; 3H); 7.14 (d; 1H); 7.06 (dt; 1H); 7.00 (d; 1H); 6.98 (dt; 1H); 6.90 (t; 1H); 5.18 (dd; 1H); 5.12 (dd; 1H); 4.82 (dd; 1H); 4.18 (dd; 1H); 3.96 (dd; 1H); 3.85 (ddd; 1H); 3.80 (ddd; 1H); 4.53 (m, 1H); 4.47 (m; 1H); 4.43 (m; 1H); 4.39 (m; 1H); 4.16 (m; 1H); 4.08 (m; 1H), 3.58 (m; 1H); 3.30 (m; 1H); 2.98 (m; 1H); 2.88 (m; 1H); 2.86 (m; 1H); 2.70 (m; 1H); 2.65 (m; 1H); 2.60 (m; 1H); 2.19 (m; 1H); 2.00 (s, 3H); 1.96 (s; 3H); 1.90 (s; 3H), 1.73 (s; 3H); 1.65 (m; 1H); 1.52 (m; 1H); 1.37 (m; 1H); 0.92 (d; 3H); 0.85 (d; 3H).

EXAMPLE 8

Preparation of

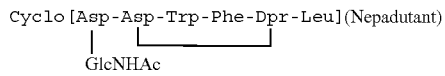
(SEQ. ID. 8)

Method a)

2 equivalents of NMM and 1.3 equivalents of TBTU and 2-acetamide-2-deoxy-β-D-glucopyranosylamine are added at 10 minute intervals to a 83 mmol/l solution in DMF of

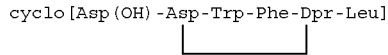

(prepared as described in Example 6).

After stirring for 1 hour at room temperature, the reaction mixture is evaporated under reduced pressure until a dense oily residue is obtained which is redissolved with a 2:8 acetonitrile-t-butoxymethane (TBME) mixture. The resulting suspension is vigorously stirred for 30 minutes at room temperature and then filtered.

The solid obtained is washed with TBME, dried under vacuum at 25-30° C. and finally purified by preparative HPLC using eluent mixtures composed of acetonitrile and water.

151 g of a white solid are obtained (titre 93.0%, yield 89.3%).

$^1$H-NMR (DMSO-d$_6$) δ:

0.85 (d; 3H); 0.92 (d; 3H); 1.36 (m; 1H); 1.51 (m; 1H); 1.65 (m; 1H); 1.76 (s; 3H); 2.16 (dd; 1H); 2.57 (dd; 1H); 2.63 (dd; 1H); 2.67 (dd; 1H); 2.83 (dd; 1H); 2.88 (dd; 1H); 2.93 (m; 1H); 3.04-3.09 (m; 2H); 3.27-3.32 (m; 2H); 3.42 (m; 1H); 3.50 (ddd+b; 2H); 3.65 (dd; 1H); 3.96 (b; 1H); 4.09 (m; 1H); 4.12 (m; 1H); 4.35 (m; 1H); 4.43 (m; 1H); 4.50 (m; 1H); 4.53 (m+t; 2H); 4.81 (dd; 1H); 4.94 (d; 1H); 4.98 (d; 1H); 6.91 (b; 1H); 6.98 (t+b; 2H); 7.06 (t; 1H); 7.14-7.17 (m; 4H); 7.24 (t; 2H); 7.27 (b; 1H); 7.33 (d; 1H); 7.42 (d; 1H); 7.77 (d; 1H); 8.05 (b; 1H); 8.10 (d; 1H); 8.51 (d; 1H); 8.77 (d; 1H); 9.00 (b; 1H); 10.84 (d; 1H).

Method b)

0.04 equivalents of 0.1 N NaOMe in MeOH are added to a 0.89 mol/l solution in

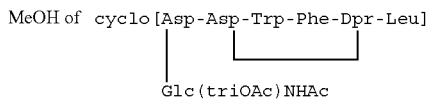

prepared as described in Example 7.

After stirring for 3 hours at room temperature the pH is corrected to 6.5-7 and Amberlyst® 15 is added. Following removal of the resin, the solution is concentrated under reduced pressure until a residue is obtained which is diluted with TBME.

The resulting suspension is filtered and the white solid obtained is washed with TBME and dried under vacuum at 35-40° C., providing a yield equal to 94.8%.

EXAMPLE 9

Preparation of of Z-Dpr(BOC)-Leu-OMe

Method a)

1.2 equivalents of NMM are added to a 0.66 mol/l solution of Z-Dpr(BOC)—OH in DMF. The solution is cooled to −25° C. and 1 equivalent of IBCF is dropped in while maintaining the temperature below −20° C.

After about 10 minutes a 0.78 mol/l pre-cooled solution containing 1 equivalent of H-Leu-OME HCl and NMM in DMF is dropped in, always maintaining the temperature below −15° C.

After stirring for one hour the reaction mixture is dropped into a 0.5 M aqueous solution of NaHCO$_3$.

The resulting suspension is filtered and the solid obtained is washed sequentially with H$_2$O, 0.05 M H$_2$SO$_4$ and H$_2$O until the pH is neutral and dried under vacuum at 30-50° C., providing a yield equal to 89.0%.

melting point 122-125° C.; $^1$H-NMR (DMSO-d$_8$) δ:

0.85 (2d; 6H); 1.37 (s; 9H); 1.40-1.71 (m; 3H); 3.01-3.36 (m; 2H); 3.61 (s; 3H); 4.06-4.37 (m; 2H); 5.03 (s; 2H); 7.35 (s; 5H); 6.66 (t; 1H); 7.20 (d; 1H); 8.29 (d; 1H).

Method b)

1 equivalent of DCC is added to a 0.35 mol/l solution of Z-Dpr(BOC)—OH in DMF containing 1 equivalent of HOSu, cooling to 0-5° C. The mixture is brought to room temperature and stirred for 1 hour. The DCC is removed by filtration and to the clear filtrate are added 1.2 equivalents of H-Leu-Ome HCl and 2.6 equivalents of NMM. After stirring for 2-3 hours at room temperature the mixture is diluted with 0.5 N NaHCO$_3$ then cooled to −5° C.

The resulting suspension is filtered and the solid obtained is washed sequentially with 0.5 N NaHCO$_3$, a 2:1 H$_2$O—DMF mixture and water, then dried under vacuum at 30-40° C., providing a yield equal to 93%.

EXAMPLE 10

Preparation of H-Dpr(BOC)-Leu-OMe

A 0.14 mol/l solution of Z-Dpr(BOC)-Leu-OMe in MeOH containing 1 equivalent of PTSA is hydrogenated at room temperature in the presence of catalytic quantities of 10% Pd/C, 50% wetness.

After reacting for about 2 hours the suspension is filtered to remove the catalyst and the filtrate is diluted with DMF.

The MeOH and the H$_2$O are completely evaporated under reduced pressure and the residual DMF solution, containing the dipeptide, is used for the subsequent coupling.

EXAMPLE 11

Preparation of Z-Phe-Dpr(BOC)-Leu-OMe

The compound was prepared from the dipeptide H-Dpr(BOC)Leu-OMe from Example 10, according to the method described in Example 9 using Z-Phe-OH.

$^1$H-NMR (DMSO-d$_6$) δ:

0.86 (2d; 6H); 1.38 (s; 9H); 1.40-1.74 (m; 3H); 2.73-3.02 (m; 2H); 3.10-3.41 (m; 2H); 3.62 (s; 3H); 4.17-4.46 (m; 3H); 4.94 (AB-Syst.; 2H); 7.18-7.39 (m; 10H); 6.52 (t; 1H); 7.52 (d; 1H); 8.13 (d; 1H); 8.25 (d, 1H).

EXAMPLE 12

Preparation of H-Phe-Dpr(BOC)-Leu-OMe

The compound was obtained from the protected derivative from Example 11, according to the method in Example 10, using DMF as the solvent.

EXAMPLE 13

Preparation of Z-Trp-Phe-Dpr(BOC)-Leu-OMe (SEQ. ID. 9)

The compound was prepared using the method in Example 9 from the tripeptide of Example 12 and using Z-Trp-OH or by coupling the two dipeptides Z-Trp-Phe-OH and H-Dpr(BOC)-Leu-OMe, obtained as described in Examples 17 and 10 respectively.

$^1$H-NMR (DMSO-d$_6$) δ:

0.86 (2d; 6H); 1.37 (s; 9H); 1.40-1.76 (m; 3H); 2.73-3.41 (m; 6H); 3.62 (s; 3H), 4.16-4.67 (m; 4H); 4.93 (AB-Syst.; 2H); 6.89-7.65 (m; 16H); 6.55 (t; 1H); 8.07 (d; 1H); 8.11 (d; 1H); 8.29 (d; 1H); 10.79 (s; 1H).

EXAMPLE 14

Preparation of Preparation of H-Trp-Phe-Dpr(BOC)-Leu-OMe (SEQ. ID. 10)

The compound was obtained from the protected derivative of Example 13, according to the method given in Example 10, using NMP as solvent.

EXAMPLE 15

Preparation of Z-Asp(OtBu)-Trp-Phe-Dpr(BOC)-Leu-OMe (SEQ. ID. 11)

Method a)

1 volume of CH$_3$CN, 1.5 equivalents of DIPEA and 1.15 equivalents of Z-Asp(OtBu)—OSu are added to a 0.16 mol/l solution of H-Trp-Phe-Dpr(BOC)-Leu-OMe in NMP, derived from the hydrogenation reaction. After stirring for 34 hours at room temperature the reaction mixture is cooled to 5° C. and is diluted with H$_2$O. The resulting suspension is filtered and the solid obtained is washed with a 3:7 CH$_3$CN—H$_2$O mixture and with H$_2$O and then dried under vacuum at 30-50° C., providing a yield equal to 90%.

Method b)

1 equivalent of DIPEA, 1.1 equivalents of TBTU and after 5 minutes 1 equivalent of the 0.25 mol/l H-Dpr(BOC)-Leu-OMe solution in DMF derived from the hydrogenation reaction (example 10), are added to a 0.22 mol/l solution of Z-Asp-(OtBu)-Trp-Phe-OH in DMF cooled to −5° C., maintaining the temperature below −5° C.

After stirring for about 2 hours the reaction mixture is diluted with a 0.5 M aqueous solution of NaHCO$_3$.

The resulting suspension is filtered and the solid obtained is washed sequentially with H$_2$O, a 3:4 DMF −0.5 M NaHCO$_3$ mixture in H$_2$O, H$_2$O and then dried under vacuum at 30-40° C. providing a yield of 84.4%.

melting point 215-218° C.; $^1$H-NMR (DMSO-d$_6$) δ:
0.86 (2d; 6H); 1.34 (s; 9H); 1.37 (s; 9H), 1.40-1.72 (m; 3H); 2.23-2.67 (m; 2H); 2.71-3.39 (m; 6H); 3.62 (s; 3H); 4.23-4.58 (m; 5H); 5.01 (AB-Syst., 2H); 6.89-7.58 (m; 16H); 6.50 (t; 1H); 7.87-8.29 (4d; 4H); 10.78 (s; 1H).

EXAMPLE 16

Preparation of Z-Trp-Phe-OMe

The compound was prepared according to the method of Example 9, coupling the two amino acids Z-Trp-OH and H-Phe-OMe.

$^1$H-NMR (CDCl$_3$) δ:
2.88-2.98 (m; 2H); 3.11 (dd; 1H); 3.32 (dd; 1H); 3.62 (s; 3H); 4.40-4.58 (m; 1H); 4.16-4.30 (m; 1H); 5.11 (s; 2H); 5.45 (d; 1H), 6.11 (d; 1H); 6.72-6.85 (m; 2H), 6.92-7.46 (m; 12H); 7.67 (d; 1H); 8.03 (s; 1H).

EXAMPLE 17

Preparation of Z-Trp-Phe-OH

The compound was prepared from the methylester of Example 16, according to the method described in Example 3.

$^1$H-NMR (DMSO-d$_6$) δ:
2.70-3.15 (m; 4H); 4.20-4.36 (m; 1H); 4.38-4.55 (m; 1H); 4.92 (s; 2H); 6.85-7.42 (m; 15H); 7.63 (d; 1H); 8.26 (d; 1H); 10.81 (s; 1H); 12.30 (b; 1H).

EXAMPLE 18

Preparation of H-Trp-Phe-OH

The compound was prepared from the protected derivative of Example 17, in accordance with the method of Example 10, using acetic acid as solvent.

EXAMPLE 19

Preparation of Z-Asp(OtBu)-Trp-Phe-OH

The compound was prepared in accordance with the method of Example 15 (method a) from the dipeptide of Example 18.

$^1$H-NMR (DMSO-d$_6$) δ:
1.35 (s; 3H); 2.21-2.67 (m; 2H); 2.71-3.18 (m; 4H); 4.22-4.58 (m; 3H); 5.00 (AB-Syst.; 2H); 6.87-7.43 (m; 14H); 7.55 (m; 2H); 7.94 (d; 1H); 8.17 (d; 1H); 10.80 (s; 1H); 12.25 (b; 1H).

---

The invention claimed is:

1. A process for preparing a bicyclic glycopeptide compound of formula (I-A)

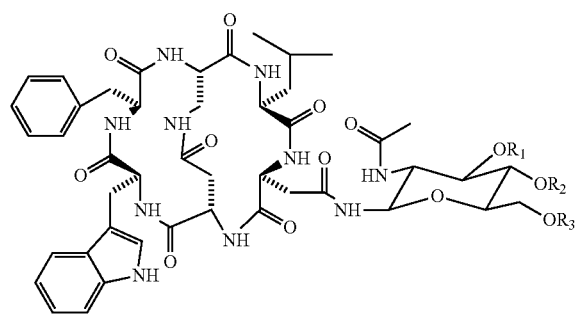

wherein $R_1$, $R_2$ and $R_3$, equal or different from each other, can be hydrogen or an oxygen protecting group, selected from the group consisting of —$COR_4$ wherein $R_4$ is selected from the group consisting of a linear or branched C1-C4 alkyl group, phenyl and phenyl substituted with a halogen atom, benzyl or benzoyl, comprising the following steps:

1A) activation of the bicyclic peptide compounds of formula (I) with a suitable coupling agent selected from the group consisting of isobutyl chloroformate, a carbodiimide and a carbodiimide in combination with a hydroxy containing compound, phosphonium salts, N-oxide guanadine salts or uranium salts of to obtain a derivative of formula (II-A)

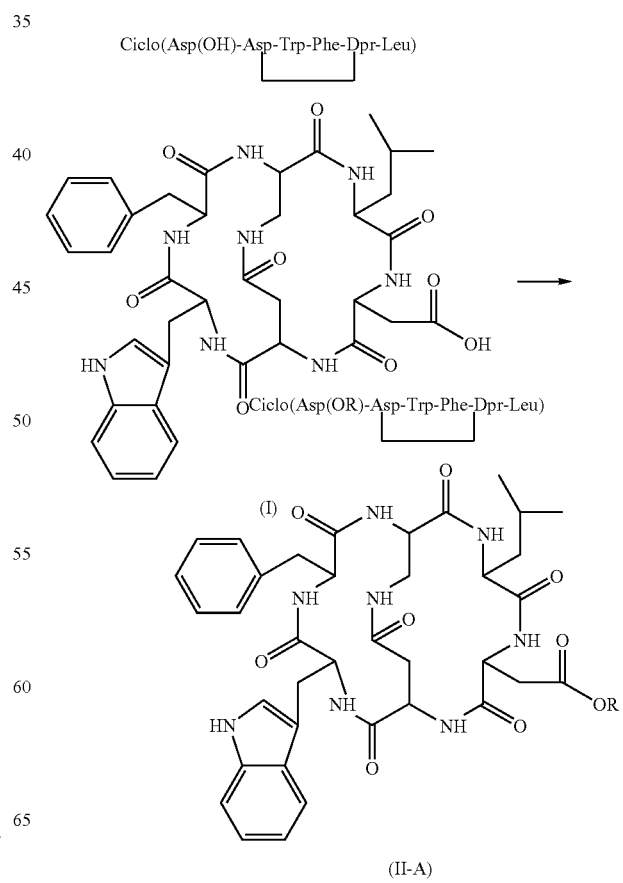

wherein R is a member selected from group consisting of benzotriazole, azabenzotriazole, succinimidy and benzotriazole substituted with a halogen;

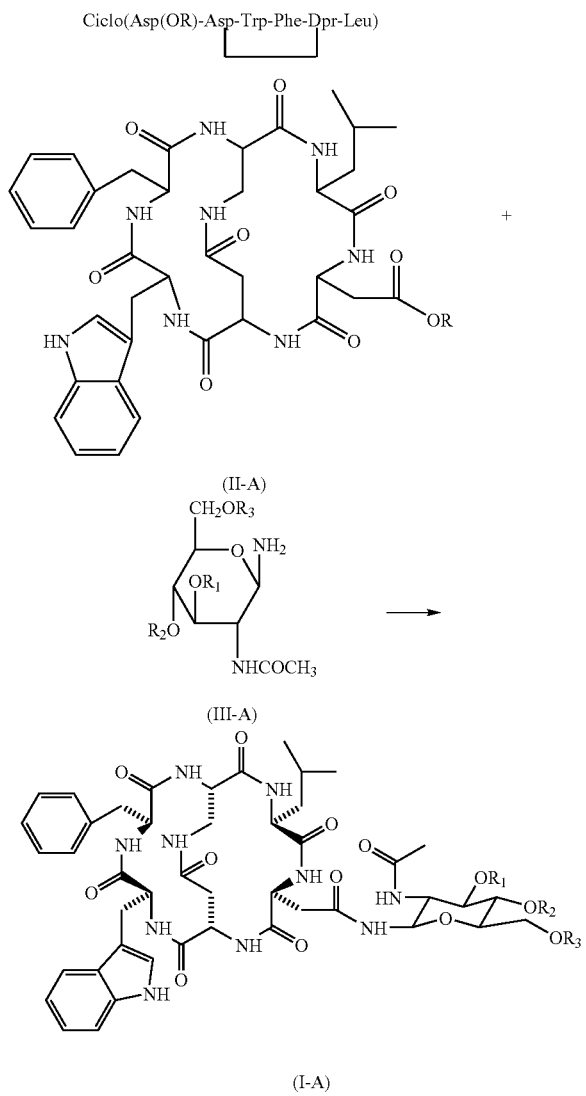

2A) reaction of the compound of formula (II-A) deriving from step 1A) in the presence of a solvent with the glycosidic derivative of formula (III-A)
wherein R, $R_1$, $R_2$, $R_3$ are defined as above.

2. The process according to claim 1, wherein the compounds of formula (I-A) wherein $R_1$, $R_2$ and $R_3$ are different from H, are transformed into the corresponding compounds of formula (I-A) wherein $R_1$=$R_2$=$R_3$=H, by a deprotection reaction in the presence of a solvent.

3. The process according to claim 1, wherein said C1-C4 alkyl group is selected from the group consisting of methyl, ethyl, propyl, butyl, isopropyl and t-butyl.

4. The process according to claim 3, wherein said C1-C4 alkyl group is methyl.

5. The process according to claim 1, wherein said glycosidic derivatives of formula (III-A) are selected from the group consisting of 2-acetamide-2-deoxy-β-D-glucopyranosylamine and 2-acetamide-3,4,6-tri-O-acetyl-2-deoxy-β-D-glucopyranosylamine.

6. The process according to claim 1, wherein said coupling agent is selected from the group consisting of isobutyl chloroformate, a carbodiimide and a carbodiimide in combination with a hydroxy containing compound, phosphonium salts, N-oxide guanidine salts or uronium salts.

7. The process according to claim 6, wherein said carbodiimides are selected from dicyclohexylcarbodiimide and 1-ethyl-3-(3-dimethylaminopropyl)carbodiimide hydrochloride; said hydroxy derivative is selected from 1-hydroxybenzotriazole, 6-chloro-1-hydroxybenzotriazole, hydroxysuccinimide and 1-hydroxy-7-azabenzotriazole; said phosphonium salts, N-oxide guanidine salts and uronium salts are selected from (Benzotriazol-1-yloxy)tri(dimethylamino)phosphonium hexafluorophosphate, (Benzotriazol-1-yloxy)tripyrrolidine phosphonium hexafluorophosphate, 1-[bis(dimethylamino)methylene]-1H-benzotriazolium-3-oxide hexafluorophosphate, 1-[bis(dimethylamino)methylene]-5-chloro-IH-benzotriazolium-3-oxide hexafluorophosphate, 1-[bis(dimethylamino)methylene]-1H-benzotriazolium-3-oxide tetrafluoroborate, 1-[bis(dimethylamino)methylene]-1H-1,2,3-triazole[4,5-b]pyridinium-3-oxide hexafluorophosphate, 1-[bis(dimethylamino)methylene]-5-chloro-1H-benzotriazolium-3-oxide tetrafluoroborate, O-[(ethoxycarbonyl)cyanomethylenamino]-N,N,N',N'-tetramethyluronium tetrafluoroborate, O-(bicyclo[2.2.1]hept-5-ene-2,3-dicarboximido)-N,N,N',N'-tetramethyluronium tetrafluoroborate, and O—(N-succinimidyl)-N, N,N,Nt-tetramethylumnium tetrafluoroborate.

8. The process according to claim 1, wherein said coupling reactions are carried out in the presence of a tertiary amine in an organic solvent at a temperature comprised between −20 and +50° C.

9. The process according to claim 8, wherein said tertiary amine is selected from the group consisting of N-methylmorpholine, triethylamine and diisopropylethylamine, and said organic solvent is selected from the group consisting of ethyl acetate, dimethylformamide and N-methylpyrrolidone.

10. The process according to claim 2, wherein said deprotection reactions are carried out by hydrogenation in the presence of a catalyst in a solvent selected from solvents which dissolve the components of the reaction without reacting with them, excluding ketones and solvents which poison the catalyst, at a temperature comprised between −20 and +50° C.

11. The process according to claim 10, wherein said catalyst is selected from 5% and 10% Palladium and said solvent is selected from dimethylformamide, N-methylpyrrolidone, acetic acid, p-toluenesulfonic acid, methanol, ethanol, isopropanol, and mixtures thereof.

12. The process according to claim 2, wherein said deprotection reactions are carried out by means of treatment with pure acids or with acids mixed with solvents, at a temperature comprised between −20 and +50° C.

13. The process according to claim 12, wherein said acids are selected from hydrochloric acid, trifluoroacetic acid and formic acid.

14. The process according to claim 2, wherein said deprotection reactions are carried out by means of treatment with a base compound in the presence of a solvent, at a temperature comprised between −20 and +50° C.

15. The process according to claim 14, wherein said base compound is selected from hydroxides of alkali metals or alkaline earth metals, and said solvent is selected from the group consisting of water, dioxane, acetonitrile, methanol, ethanol, isopropanol, and mixtures thereof.

* * * * *